United States Patent [19]
Vrba

[11] Patent Number: 5,122,518
[45] Date of Patent: Jun. 16, 1992

[54] INSECTICIDES

[76] Inventor: Cenek H. Vrba, 213 Cardiff Dr. N.W., Calgary, Alta, Canada, T2K 1S1

[21] Appl. No.: 422,505

[22] Filed: Oct. 17, 1989

[30] Foreign Application Priority Data

Oct. 19, 1988 [DE] Fed. Rep. of Germany ....... 3835592

[51] Int. Cl.⁵ ...................... A01N 55/00; A01N 25/00
[52] U.S. Cl. ........................................ 514/63; 514/770
[58] Field of Search .............. 514/63, 465, 770; 424/724

[56] References Cited

U.S. PATENT DOCUMENTS

| | | | |
|---|---|---|---|
| 2,818,340 | 12/1957 | Goddin et al. | 426/96 |
| 3,124,505 | 3/1964 | Doyle et al. | 424/724 |
| 3,159,536 | 12/1964 | Marotta | 424/600 |
| 3,235,451 | 2/1966 | Odeneal | 424/724 |
| 3,964,649 | 6/1976 | Alexander | 222/399 |
| 4,279,895 | 7/1981 | Carle | 424/724 |
| 4,632,936 | 12/1986 | Boase et al. | 514/770 |

FOREIGN PATENT DOCUMENTS

| | | | |
|---|---|---|---|
| 674442 | 4/1966 | Belgium. | |
| 978853 | 12/1975 | Canada | 167/3 |
| 0110564 | 10/1983 | European Pat. Off. . | |
| 1133210 | 12/1965 | United Kingdom . | |

OTHER PUBLICATIONS

Chemical Abstracts vol. 84:146150e (1976).
Chemical Abstracts vol. 101:85710h (1984).
J. Econ. Ent Article 52:190-207, Apr. 1959.
Vrba, C. H., et al., "The effect of silica aerogel on the mortality of *Tribolium confusum* (Duval) as a function of exposure time and food deprivation", *Canadian Journal of Zoology* (1983), vol. 61, pp. 1481–1486.

Primary Examiner—Frederick E. Waddell
Assistant Examiner—K. Weddington
Attorney, Agent, or Firm—Beveridge, DeGrandi & Weilacher

[57] ABSTRACT

Insects are combatted by treating the insects with a pyrogenically produced and hydrophobic silica. The insects can be sprayed with an aqueous dispersion of the pyrogenically produced and hydrophobic silica. Alternatively, the insects can be dusted with the silica in powdery form.

5 Claims, No Drawings

INSECTICIDES

INTRODUCTION AND BACKGROUND

The present invention relates to a method of controlling insects.

It is known that harmful insects can be combatted on plants by spraying various organic substances. These organic substances however, while being effective against the insects, have the disadvantage that they generally exhibit a high toxicity for other life forms too and may also be environmentally damaging in that they are not biodegradable.

There was thus the problem of finding an insecticide which is not toxic in these respects.

SUMMARY OF THE INVENTION

An object of the invention is to provide a method of combatting insects which is characterized in that the insects are treated with a pyrogenically produced, hydrophobic silica.

In a preferred embodiment of the invention, the insects can be sprayed with an aqueous dispersion of the pyrogenically produced, hydrophobic silica.

In another preferred embodiment of the invention, the insects can be dusted with the powdery, pyrogenically produced, hydrophobic silica.

The aqueous dispersion can exhibit a content of pyrogenically produced, hydrophobic silica of 0.2 to 20% by weight, preferably 3 to 16% by weight.

The following silica, characterized by physical and chemical parameters, can be used as pyrogenically produced and hydrophobic silicas. The trademark "Aerosil" is owned by Degussa AG.

These silicas can be produced according to known methods such as e.g. according to DE-PS 11 63 784, incorporated herein by reference. It can be seen from the table that the surface areas range from 90+20 to 260+30 m$^2$/g with an average primary particle size of 7-16 nanometers. The pH of such products ranges from 3.4 to 7.5.

The method of the invention exhibits the following advantages:

The dispersions of pyrogenically produced and hydrophobic silicas used and these silicas themselves are non-toxic and not dangerous to the environment with the exception of insects. They do not leave any undesirable residues on plants, in foodstuffs, etc. There are no storage problems and no problems e.g. with overdosing. The powdery layer on leaves or plants can be readily removed by washing with water.

A further advantage is the destructive action on Gr− and Gr+ bacteria.

The method of the invention can be used with advantage in the construction industry, gardening, agriculture, medicine and in veterinary medicine.

The pesticidal action of the silica dispersions or of dry water used in accordance with the invention is based on a direct topical contact of these substances with the insects.

This contact should last for a fairly long time, preferably for several hours. The dispersions or these silicas themselves are applied in a sufficient measure on the plants until a visible, thin layer can be seen.

Where unfavorable wind conditions render an application of the silica onto leaves unfavorable, the dispersion can also be buried in the ground, advantageously at a depth of 2 to 4 cm. In this way, the silica forms a barrier to prevent insect; e.g. larvas attack on the roots.

This method of use has the advantage that the retention capacity of the soil can be improved by the silica.

| Testing Method | DIM | AEROSIL R 202 | AEROSIL R 805 | AEROSIL R 812 | AEROSIL R 972 | AEROSIL R 974 |
|---|---|---|---|---|---|---|
| Behavior towards water | | | | hydrophobic | | |
| Appearance | | | | | | |
| Surface according to BET[1] | m$^2$/g | 90 ± 20 | 150 ± 25 | 260 ± 30 | 110 ± 20 | 170 ± 20 |
| Average size of the primary particles | nanometers | 14 | 12 | 7 | 16 | 12 |
| Stamping density[2] | | | | | | |
| Normal product | g/l | ca. 50 | ca. 50 | ca. 50 | ca. 50 | ca. 50 |
| Compressed product (additive "V") | g/l | ca. 90 | ca. 90 | ca. 90 | ca. 90 | ca. 90 |
| Drying loss[3] (2 hours at 105° C. upon leaving the supplier) | % | <0.5 | <0.5 | <0.5 | <0.5 | <0.5 |
| Ignition loss[4][7] (2 hours at 1000° C.) | % | 4.5-7.5[13] | 6-9[14] | 1.0-2.5[15] | <2[12] | <2[12] |
| pH[5] (in 4% aqueous dispersion) | | 4-6[10] | 3.5-5.5[10] | 5.5-7.5[10] | 3.6-4.3[10] | 3.4-4.2[10] |
| SiO$_2$[8] | % | >99.8 | >99.8 | >99.8 | >99.8 | >99.8 |
| Al$_2$O$_3$[8] | % | <0.05 | <0.05 | <0.05 | <0.05 | <0.05 |
| Fe$_2$O$_3$[8] | % | <0.01 | <0.01 | <0.01 | <0.01 | <0.01 |
| TiO$_2$[8] | % | <0.03 | <0.03 | <0.03 | <0.03 | <0.03 |
| HCl[8][11] | % | <0.025 | <0.025 | <0.025 | <0.05 | <0.1 |
| Sieve residue[6] (according to Mocker, 45 μm) | % | — | — | — | — | — |

[1] according to DIN 66 131
[2] according to DIN ISO 787/XI, JIS K 5101/18
[3] according to DIN ISO 787/II, ASTM D 280, JIS K 5101/21
[4] according to DIN 55 921, ASTM D 1208, JIS K 5101/23
[5] according to DIN ISO 787, IX, ASTM D 1208, JIS K 5101/24
[6] according to DIN ISO 787/XVII, JIS K 5101/20
[7] relative to the substance dried 2 hours at 105° C.
[8] relative to the substance annealed 2 hours at 1000° C.
[9] special anti-moisture packaging
[10] in water: acetone or methanol = 1:1
[11] HCl content is a component of the ignition loss
[12] contains approximately 1% chemically bound carbon
[13] contains approximately 5% chemically bound carbon
[14] contains approximately 7% chemically bound carbon
[15] contains approximately 3.5% chemically bound carbon.

In a special embodiment, a piece of fabric, e.g. linen, can be impregnated with the silica dispersion and set between rows of plants. In this embodiment, the silica dispersion is applied to the fabric in sufficient thickness to form an adhering coating on the fabric; e.g. burlap. To prevent loss by wind carrying the produced silica away, the fabric can be partially buried or immersed in the soil.

In another embodiment, the fabric impregnated with the silica dispersion can be cut into strips and applied directly to the plants, e.g. tree crowns and trunks.

DETAILED DESCRIPTION OF THE INVENTION

The following examples are illustrative of the present invention.

So-called "dry water" with an Aerosil content of 20 by weight was prepared with Aerosil R 972 and water as a supply. This means that water is dispersed into the powdery silica. The bulk of the silica is so great that the water forms the discontinuous phase and stays dispersed in droplets in the silica. Up to 90% water can be dispersed into the silica in this way.

Low concentrations, e.g. 15% by weight Aerosil R 972, suspended in water result in a paste. This paste forms a thick, broken layer after drying and a thin film of powdery material thereunder.

The 15% paste can be diluted with water to a concentration of 4%, or lower, by weight. This suspension is sprayed onto the bottom of a Petri dish with a known spraying device, dried in the course of 24 hours and tested for insecticidal action. The insects were placed into the Petri dish.

First, a 15% dispersion and therefrom a 4% suspension were produced in the same manner with Aerosil R 974.

Table 1 shows the results of the investigation of the insecticidal action in 14 examples.

pods. Generally no insects resistant to inert sorptive dusts have been discovered and reported within last 35 years.

The hydrophobic silica can be used in veterinary (human) medicine in the treatment of the following ectoparasitic conditions:

1. Spined Rodent Louse—*Polyplax Spinulosa* in rats.
2. Ear mites—*Psoroptes Cuniculi* in rabbits and cats.
3. Fleas—*Ctenocephalides Felis et Canis*—in cats and dogs.
4. Biting Dog Louse—*Trichodectes Canis*—in dogs.
5. Brown Dog Tick—*Rhipicephalus Sanguineus*—in dogs.
6. Short Nose Cattle Louse—*Haematopinus Eurysternus*—in cattle.
7. Cattle Tail Louse—*Haematopinus Quadripertus*—in cattle.
8. Spinose Ear Tick—*Otobius Megnini*—in cattle, horses and mules.
9. Cattle Biting Louse—*Bovicola Bovis*—in cattle.
10. Red Mite—*Dermanyssus Gallinae*—in chickens.
11. Generally Lice, Mites and Ectoparasites in poultry.
12. Lice, Mites, Fleas in domestic pigeons, Lapwing Plover, Red Jungle Fowl, Western Red Shafted Flicker, Yokohama Chicken, Golden Pheasant, Mocking Bird, Quail, Peacock, Ring Necked Pheasant, White Turkey, Canaries, Parrots, Parakeets, Ducks, Geese, Condors.
13. Snake Mites—*Ophionyssus Natricis*—in snakes.
14. Crab Louse—*Phtirius Pubis*—in humans.
15. Bedbugs—*Cimex Lactulerius*—in humans and animals.

Generally, dosages are not critical, sufficient silicas being used to contact the insect. If greater amounts are used the effect is essentially the same. There is no progressive effect beyond the minimum needed to obtain the necessary effect. Thus for flour beetles an amount of

TABLE 1

Continuous exposure of *Tribolium confusum duv.* (flour beetle) to Aerosil R 972 and R 974

| Example | Material Tested | Dosage mg | No. of Insects | Cumulative Mortality in days in % | | | | | | |
|---|---|---|---|---|---|---|---|---|---|---|
| | | | | 1 | 2 | 3 | 4 | 5 | 6 | 7 |
| 1 | Aerosil R 972 | 100 | 10 | 50 | 80 | 100 | | | | |
| 2 | Aerosil R 972 | 100 | 30 | 0 | 53 | 100 | | | | |
| 3 | Aerosil R 972 4% susp. dehydrated | 15 | 30 | 0 | 70 | 97 | 97 | 97 | 97 | 100 |
| 4 | like No. 3 | 15 | 30 | 0 | 70 | 97 | 97 | 100 | | |
| 5 | like No. 3 | 15 | 30 | 0 | 57 | 93 | 93 | 97 | 100 | |
| 6 | untreated reference | — | 30 | 0 | 0 | 0 | 0 | 0 | 0 | |
| 7 | Aerosil R 972 15% susp. dehydrated | 300 | 30 | 0 | 97 | 100 | | | | |
| 8 | like No. 7 | 100 | 30 | 0 | 90 | 97 | 100 | | | |
| 9 | Aerosil R 974 | 100 | 10 | 100 | | | | | | |
| 10 | Aerosil R 974 | 100 | 30 | 80 | 100 | | | | | |
| 11 | Aerosil R 974 4% susp. dehydrated | 15 | 30 | 80 | 100 | | | | | |
| 12 | like No. 11 | 15 | 30 | 80 | 100 | | | | | |
| 13 | like No. 11 | 15 | 30 | 70 | 100 | | | | | |
| 14 | untreated reference | — | 30 | 0 | 0 | 0 | 0 | 0 | 0 | |

The hydrophobic silica as described herein after sufficient exposure of insect is insecticidal to the entire class of Insecta (Hexapoda) including their developmental stages but excepting eggs. After a limited exposure of insects to hydrophobic silica, a generally deterring to partially insecticidal action is obtained, depending on the time of exposure. The hydrophobic silica also is detrimental to some other classes of arthropods like e.g. Crustacea—sowbugs; Arachnida—mites, ticks, spiders and some other economically less important arthro- 1 mg per 15 beetle was sufficient, where each beetle weighed about 1 mg. This is equal to about 0.06 mg silica/mg insect weight.

Further modifications and variations will be apparent to those skilled in the art from the foregoing and are intended to be encompassed by the appended claims.

I claim:

1. A method of killing insects comprising contacting an insect in any developmental stage except eggs with an insecticidally sufficient amount to cause non-chemical, physical damage with 100% mortality to said insect of an aqueous dispersion of pyrogenically produced and hydrophobic silica as the sole insecticide, wherein said silica is non-toxic for other life forms in the environment.

2. The method according to claim 1, wherein the insect is sprayed with an aqueous dispersion of the pyrogenically produced and hydrophobic silica.

3. The method according to claim 1 wherein the amount of silica used in at least about 0.06 mg silica/mg insect weight.

4. The method according to claim 1 wherein the silica has the following characteristics:
Surface area (BET: $90 + 20$ to $260 + 30$ m$^2$/g
Average primary particle size: 7–1 nanometers
pH: 3.4–7.5.

5. A method of killing insects consisting essentially of contacting an insect in any developmental stage except eggs with an insecticidally sufficient amount to cause non-chemical, physical damage with 100% mortality to said insect of an aqueous dispersion of pyrogenically produced and hydrophobic silica as the sole insecticide.

* * * * *